United States Patent [19]

Demeyere et al.

[11] Patent Number: 4,933,096

[45] Date of Patent: Jun. 12, 1990

[54] IMIDAZOLE COMPOUNDS AND TEXTILE TREATMENT COMPOSITIONS CONTAINING THEM

[75] Inventors: Hugo J. M. Demeyere, Merchtem, Belgium; Frederick E. Hardy, New Castle Upon Tyne, England; Axel Koenig, Wemmel, Belgium

[73] Assignee: The Procter & Gamble Company, Cincinnati, Ohio

[21] Appl. No.: 314,673

[22] Filed: Feb. 22, 1989

[30] Foreign Application Priority Data

Feb. 26, 1988 [GB] United Kingdom ............... 8804555

[51] Int. Cl.$^5$ ............................... D06M 13/352
[52] U.S. Cl. .................... 252/8.8; 548/335; 548/341
[58] Field of Search .............. 548/341, 335; 252/8.8

[56] References Cited

U.S. PATENT DOCUMENTS 4,724,089  2/1988  König et al. ............... 252/8.8
4,806,255  2/1989  König et al. ............... 252/8.8

OTHER PUBLICATIONS

Chemical Abstracts, 108:168981t (1988)[EP 251,760, Hirata et al., 1/7/88].
Chemical Abstracts, 110:9575p (1989)[JPN. Kokai Tokkyo Koho JP 63, 130,647, Hirata et al., 6/2/88].
Chemical Abstracts, 110:174419y (1989)[JPN. Kokai Tokkyo Koho 63,210,161, Niino, 8/31/88].
Chemical Abstracts, 108:224125f (1988)[EP 259,266, Coates et al., 3/9/88].

Primary Examiner—Richard A. Schwartz
Attorney, Agent, or Firm—Robert B. Aylor; Richard C. Witte

[57] ABSTRACT

Novel imidazole compounds are disclosed, as well as textile treatment compositions containing said imidazole compounds and a Bronstedt acid as dispersing aid.

17 Claims, No Drawings

IMIDAZOLE COMPOUNDS AND TEXTILE TREATMENT COMPOSITIONS CONTAINING THEM

TECHNICAL FIELD

This invention relates to novel imidazole compounds, and textile treatment compositions containing such compounds.

BACKGROUND OF THE INVENTION

Textile treatment compositions suitable for providing fabric softening and static control benefits during laundering are well known in the art and have found widespread commercial application. Conventionally, rinse-added fabric softening compositions contain, as the active component, substantially water-insoluble cationic materials having two long alkyl chains. Typical of such materials are di-hardened tallow dimethylammonium chloride and imidazolinium compounds substituted with two tallow groups.

Recently, a new class of softening agents has been developed, which possess improved softening abilities. Such compounds, disclosed in EPA No. 0 199 383, are selected from di-higher alkyl cyclic amines, with the di-tallow imidazolines and ester derivatives thereof being preferred.

It has appeared however that stringent conditions need to be applied if one wants to obtain a stable, concentrated dispersion containing said cyclic-amine softening agents in the molten state; such conditions include high temperature, inert atmosphere, absence of moisture, and are therefore difficult and expensive to create, especially upon shipment of the concentrated dispersion.

These stability problems become even more acute when the said cyclic-amine softening agents are mixed with a quaternary softening agent before being dispersed in water to form the final composition.

It has now been found that by using certain novel imidazole compounds, aqueous dispersions can be formulated, which show a very good hydrolytical stability in all storage conditions.

It has further been found that such imidazole compounds are particularly suitable for pre-mixing with conventional quaternary ammonium compounds especially in terms of stability or prolonged storage.

In terms of performance, the textile treatment compositions containing said imidazole dispersions provide excellent softeness benefits to the treated fabrics.

SUMMARY OF THE INVENTION

The present invention provides novel imidazole compounds of the formula (I) hereinafter described, and stable aqueous dispersions containing from 1% to 40% of such imidazole compounds, and a dispersing aid selected from the group of Bronstedt acids having a pKa value not greater than 6.

DETAILED DESCRIPTION OF THE INVENTION

The imidazole compounds

The novel imidazole compounds of the present invention are of the formula:

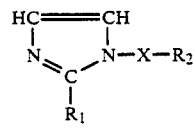

wherein $R_1$ and $R_2$ are, selected independently $C_8$–$C_{30}$ alkyl or alkenyl groups, and X is selected from the group of:

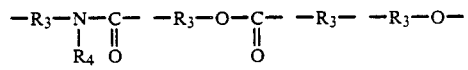

wherein $R_3$ is a $C_2$–$C_5$ alkanediyl group, or is

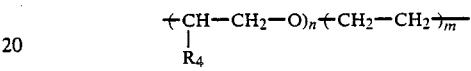

with n being an integer from 0 to 10, and m is an integer from 0 to 2, $n+m>1$, and $R_4$ being a $C_{1-4}$ alkyl group or hydrogen.

Preferred imidazole compounds

In formula (I) above, $R_1$ and $R_2$ are, preferably, $C_{12}$–$C_{20}$ alkyl groups, more preferably $C_{15}$–$C_{18}$ alkyl groups.

It is also preferred that the X group, in formula (I) above, be

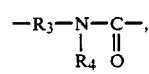

with $R_4$ being preferably hydrogen, or

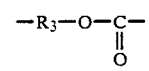

In both instances, $R_3$ should most preferably be ethanediyl.

Consequently, most preferred imidazoles, in particular for use in the textile-treatment compositions of the present invention, are of the following formulāe:

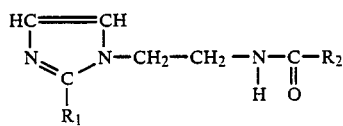

wherein $R_1$ and $R_2$ are, selected independently $C_{15}$–$C_{18}$ alkyl group or

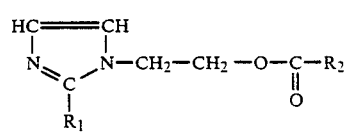

wherein $R_1$ and $R_2$ are, selected independently $C_{15}$–$C_{18}$ alkyl group.

Preparation of the imidazole compounds

The present imidazole compounds can advantageously be prepared by dehydrogenation of the corresponding imidazoline compounds.

The imidazoline compounds are made according to the following reactions:
when X is

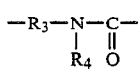

in formula (I)
A first dehydration is conducted:

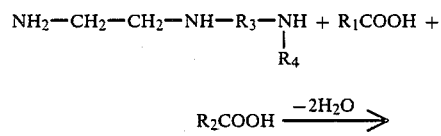

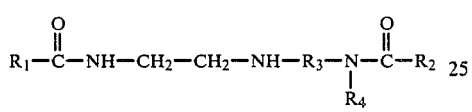

A second dehydration, typically under more stringent conditions (high temperature, vacuum) is then conducted and results in the following imidazoline:

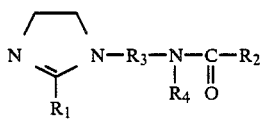

when X is

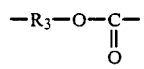

in formula (I), two successive dehydrations are also conducted:

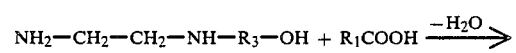

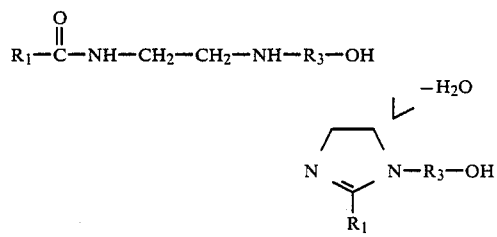

This imidazoline is then reacted with $R_2COOH$ to yield

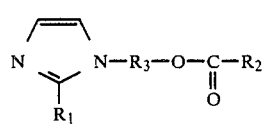

When X is $R_3$ in formula (I) the reaction is as follows:

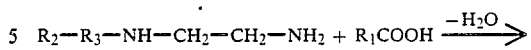

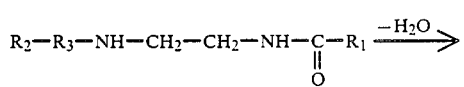

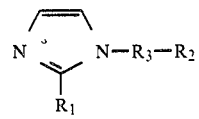

When X is $-R_3-O$ in formula (I), the reaction is as follows:

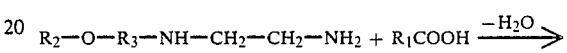

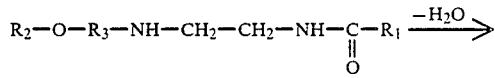

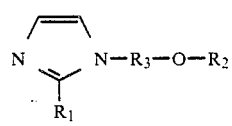

One dehydrogenation method consists of reacting the imidazoline with Palladium on carbon catalyst. Typically, a mixture of the imidazoline and stilbene is dissolved in decalin, the solution is heated to 180°, stirred with Palladium on carbon catalyst;

A second, milder, dehydrogenation route is to react the imidazoline with manganese dioxide. Typically, active manganese dioxide is added to a solution of the imidazoline in chloroform and the suspension stirred at low temperature.

Another dehydrogenation route is disclosed in U.S. Pat. No. 3,629,278 and uses a copper catalyst.

A detailed method of preparation is described in the experimental part of the present application.

The textile-treatment compositions

The textile treatment compositions of the present invention are stable aqueous dispersions, containing from 1% to 40% preferably 2% to 30% of the imidazole compounds described above, and a dispersing aid.

The dispersing aid

Bronstedt acids having a pKa value of 6 or less have been found to be excellent dispersing acids for the imidazoles of the compositions herein. Typically, the imidazole is heated to a temperature above its melting point. The melt is then slowly added to an aqueous solution of the dispersing aid under vigorous stirring or high shear mixing.

The pH of the dispersion, after mixing, is preferably in the range from 2.5 to 6, most preferably 3 to 5.

Typically, the amount of acid is from 1% to 50% by weight of the imidazole, preferably from 2% to 30%, most preferably from 5 to 20%. The dispersing aid imparts a low viscosity and excellent phase stability to the dispersions, even at high amine concentrations.

Examples of suitable dispersing aids include the inorganic mineral acids and carboxylic acids, in particular the low molecular weight carboxylic acids of the formula R—COOH (R being a $C_1$–$C_5$ alkyl group), alkylsulfonic acids of the formula R—$CH_2$—$SO_3H$ (R being a $C_1$–$C_5$ alkyl group), citric acid, and polyhydroxy acids such as gluconic acids.

Suitable inorganic acids include HCL, HBr, $H_2SO_4$, $H_2SO_3$, $HNO_3$ and $H_3PO_4$. Suitable organic acids include formic, acetic, methylsulfonic, ethylsulfonic, citric acid, gluconic acid. Preferred acids are acetic phosphoric hydrochloric, formic and methylsulfonic acid. Mixtures of above organic/inorganic dispersing aids are also suitable.

Optional quaternary ammonium salt

In addition to the imidazole compound and the dispersing aid the dispersions herein preferably further contain a conventional quaternary ammonium softening agent. Mixes of the imidazole and a conventional quaternary ammonium salt have been found to be particularly stable. Examples of conventional quaternary ammonium salts include (i) acyclic quaternary ammonium salts having the formula:

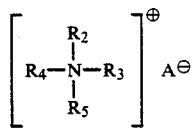

wherein $R_2$ is an acyclic aliphatic $C_{15}$–$C_{22}$ hydrocarbon group which may be interupted by ester groups. $R_3$ is a $C_1$–$C_4$ saturated alkyl or hydroxyalkyl group, $R_4$ and $R_5$ are selected from $R_2$ and $R_3$, and A is an anion. Rapidly biodegradable compounds of formula (i) where $R_2$ and possibly $R_4$, are interupted by ester groups, are disclosed in E.P.A. No. 239.910.

(ii) diamido quaternary ammonium salts having the formula:

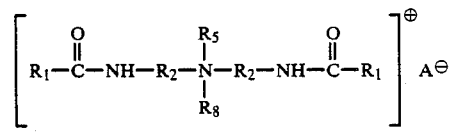

wherein $R_1$ is an acyclic aliphatic $C_{15}$–$C_{21}$ hydrocarbon group, $R_2$ is a divalent alkylene group having 1 to 3 carbon atoms, $R_5$ is selected from $R_1$ or $R_8$ and $R_8$ is a $C_1$–$C_4$ saturated alkyl or hydroxyalkyl groups, and $A^-$ is an anion:

(iii) diamido alkoxylated quaternary ammonium salts having the formula:

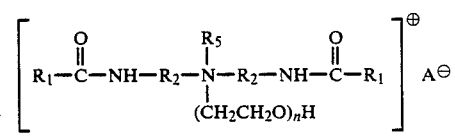

wherein n is equal to 1 to about 5, and $R_1$, $R_2$, $R_5$ and $A^-$ are as defined above;

(iv) quaternary ammonium compounds having the formula:

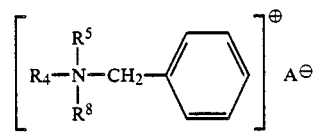

wherein $R_4$ is an acyclic aliphatic $C_{15}$–$C_{22}$ hydrocarbon group, $R_5$ and $R_8$ are as defined above, $A^-$ is an anion;

(v) quaternary imidazolinium compounds.

Examples of Component (i) which represent the preferred category dialkyldimethylammoniums salts such as ditallowdimethylammonium chloride, ditallowdimethylammonium methylsulfate, di(hydrogenated tallow) dimethylammonium chloride, distearyldimethylammonium chloride, dibehendyldimethylammonium chloride, the monoalkyltrimethylammonium salts such as monotallowtrimethylammonium chloride, mono(hydrogenated tallow) trimethylammonium chloride, palmityltrimethylammonium chloride and soyatrimethylammonium chloride, di(hydrogenated tallow) dimethylammonium chloride and ditallowdimethylammonium chloride are preferred.

Examples of Component (ii) are methylbis(tallowamidoethyl) (2-hydroxyethyl) ammonium methylsulfate and methylbis (hydrogenated tallowamidoethyl) (2-hydroxyethyl) ammonium methylsulfate wherein $R_1$ is an acyclic aliphatic $C_{15}$–$C_{17}$ hydrocarbon group, $R_2$ is an ethylene group, $R_5$ is a methyl group, $R_8$ is a hydroxyalkyl group and A is a methylsulfate anion; these materials are available from Sherex Chemical Company under the trade names Varisoft (®) 222 and Varisoft (®) 110, respectively.

An example of Component (iv) is dimethylstearylbenzylammonium chloride wherein $R_4$ is an acyclic aliphatic $C_{18}$ hydrocarbon group, $R_5$ is a methyl ·group, $R_5$ is a methyl group and A is a chloride anion, and is sold under the trade names Varisoft (®) SDC by Sherex Chemical Company and Ammonyx ® 490 by Onyx Chemical Company.

Examples of (v) are 1-methyl-1-tallowamido-ethyl-2-tallowimidazolinium methylsulfate and 1-methyl-1-(hydrogenated tallowamidoethyl)-methylsulfate. The quaternary ammonium compounds are preferably used at levels in the range of from 0.5% to 15%. The ratio (quaternary ammonium salt):(imidazole) should not exceed 10:1, and preferably does not exceed 2:1.

Other optional softening agents

It may be appropriate to use, in combination with the imidazole herein, or with the imidazole/quaternary ammonium mixture hereinabove described, certain softening agents which are the reaction products of a polyamine with a high fatty acid such as described in E.P.A. No. 199 383.

The preferred species is ditallow imidazoline, which has the formula:

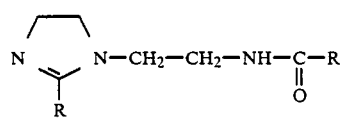

with R being a $C_{16-18}$ alkyl group.

Optional co-softening agents

The co-softening agents for use herein can be selected from fatty acid esters of polyhydric alcohols having up to 8 carbon atoms such as described in DE-A-26 31 114. Examples of the like esters include sorbitan esters and glycerol esters such as sorbitan monostearate, sorbitan monooleate, glycerol mono-di- and tri-fatty acid esters wherein the acid is selected from stearic, oleic, lauric, capric, caprylic, caproic, valeric, butyric, propionic and acetic acid; an individual glycerol can be esterified by identical fatty acid groups or by mixed esters e.g. glycerol monostearatedioleate. Polyethyleneglycol esters monostearate, wherein the polyethyleneglycol moiety has a molecular weight in the range from 200 to 400 are also included in that class. Fatty acid esters of monohydric alcohols having at least 4 carbon atoms such as isobutyl stearate and ethyl hexyl stearate can also be useful.

Additional co-softening agents which can be used are: glycerol, diglycerol, ethylene glycol, propylene glycol, diethylene glycol, dipropylene glycol, dihexylene glycol, polyethylene glycol (MW 200–100.000), polypropylene glycol (MW 200–100.000), polyvinylalcohol, polyoxyethylenepolyoxypropylene copolymers, polypropylene glycol (MW 900), glucose methylether, butyldiglycolether, diethyleneglycolmonobutylether, propyleneglycolmonoethyl or ethyl ether, ethylene carbonate, propylene carbonate.

Useful also are alkylpolyglucosides of the general formula $R^2O(CnH_{2n}O)_t$ (glucosyl)$_x$ wherein $R^2$ is alkyl, alkylphenyl, hydroxyalkyl, hydroxyalkylphenyl and mixture thereof wherein the alkyl chain has from 8 to 18 carbon atoms, t is from 0 to 2 and x from 2 to 7, can also be used in the composition. These glucosides exhibit desirable solvent properties and in addition can confer fiber benefits such as softness.

Lanolins and derivatives and paraffins having from 16 to 30 carbon atoms contitute another example of non-ionic agents which can be used if desired. Low melting oils from animal, vegetable or mineral origin are representative of this class of materials. Carnation oil ®, Jojoba oil ® and Sunflower oil are specific examples which are found to work.

Another important class of emulsifying agents is represented by materials of the general formula:

$$R_1COOR_2$$

wherein $R_1$ is a straight or branched chain alkyl or alkenyl group having from 8 to 23 carbon atoms and $R_2$ is hydrogen or an alkyl or hydroxyalkyl group having 1–4 carbon atoms.

Highly preferred materials of this class are the $C_{10}$ to $C_{20}$ saturated fatty acids, especially lauric acid, myristic acid, palmitic acid and stearic acid.

Clay materials such as the low ion-exchange-capacity ones described in EPA No. 150.531 can also be used.

Preferred among the co-softening agents above, are glycerol esters, fatty alcohols, alkoxylated fatty alcohols and fatty acids.

The co-softening agents above can be used in combination with cation-active amines, namely primary, secondary and tertiary amines having, at least, one straight-chain organic group of from 12 to 22 carbon atoms. Preferred amines of this class are ethoxyamines, such as monotallow-dipolyethoxyamine, having a total of 2 to 30 ethoxygroups per molecule. Suitable are also ditallow-N,N', N'-tris (2-hydroxyethyl)-1,3-propylenediamine, or $C_{16-18}$-alkyl-N-bis(2-hydroxyethyl) amines, examples of above amines are these sold under the trade name GENAMIN C, S, D, and T, by Hoechst.

The co-softening agents above are used at ratios of from 5:1 of 20:1 of main softening agent to co-softening agent.

Silicone Components

The compositions herein can optionally contain from 0 to 10% of an aqueous emulsion of a predominantly linear polydialkyl or alkyl, aryl siloxane in which the alkyl groups can have from one to five carbon atoms and may be wholly or partially fluorinated. Suitable silicones are polydimethyl siloxanes having a viscosity at 25° C. in the range from 100 to 100,000 centistokes, preferably in the range from 1000 to 12,000 centistokes.

The silicone component suitable for use herein is more fully described in British Pat. No. 1.549.180.

Organic solvent

Low levels of organic solvents may be used in the formulation of the present compositions, in amount of less than 10%, preferably less than 2%.

Electrolyte

In order to further improve the stability of the compositions herein, and further adjust their viscosities, these compositions can contain relatively small amounts of electrolyte. A highly preferred electrolyte is $CaCl_2$. It has been found that the Brookfield viscosities of highly concentrated dispersions can be reduced to less than 100 cps, using relatively small amounts of $CaCl_2$ (e.g., 600 ppm).

Others

The compositions herein can optionally contain other ingredients known to be suitable for use in textile softeners. Such adjuvents include perfumes, preservatives, germicides, colorants, dyes, fungicides, stabilizers, brighteners and opacifiers. These adjuvents, if used, are normally added at their conventional levels. However, in the case of composition ingredients utilized for a fabric treatment effect, e.g., perfumes, these materials can be added at higher than normal levels, corresponding to the degree of concentration of the product.

EXPERIMENTAL PART

1. Preparation of ditallowimidazole (1-tallowamido-ethyl-2-tallowimidazole)

Ditallowimidazole is a compound of formula I with X being $$\begin{array}{c} R_3-N-C, \\ | \quad \; \|  \\ R_4 \quad O \end{array}$$

$R_1$ and $R_2$ being $C_{16-18}$ (tallow) alkyl groups, $R_3$ being ethanediyl, $R_4$ being hydrogen.

a: Preparation of the imidazoline

Synthesis was conducted according to the reaction given in the description of the present invention: diethylene-triamine was reacted with $C_{16-18}$ tallow acid and a first dehydratation took place at 90° C. A second dehydration then took place on the obtained intermediate product (1–3 ditallowamidoamine) at 190° C. and under vacuum. Ditallowimidazoline was obtained (1-tallowamidoethyl-2-tallowimidazoline).

b: Preparation of the imidazole

The ditallowimidazole was then obtained by dehydrogenation of the ditallowimidazoline. The detailed method is as follows.

5 gr of ditallowimidazoline and 3 gr of stilbene (as proton acceptor) were dissolved in 30 ml decalin.

The mixture was heated to 150° C. and stirred with 200 mgr Pd on Carbon catalyst. After 24 hrs. an extra 100 mgr of Pd/C catalyst was added. Total reaction time was 48 hours.

The formed ditallow-Imidazole was filtered off and washed with diethylether and benzene.

Gross yield of the reaction was about 50%. Melting point of the reaction product was about 80° C.

2. Textile softening compositions containing the ditallow-imidazole

The following compositions were prepared. Example III and IV represent concentrated compositions to be used as is or to be diluted in water before use.

| Ingredient | Ex. I | Ex. II | Ex. III | Ex. IV |
|---|---|---|---|---|
| Ditallowimidazole | 5% | 3.0% | 8% | 15% |
| Ditallowdimethylammoniumchloride | — | 2.0% | 4% | 1.0% |
| PDMS* | — | — | 1% | 1% |
| Hydrochloric acid | — | 0.2% | 0.8% | 1.0% |
| Acetic acid | 0.5% | — | — | — |
| Calcium chloride | — | — | 0.02% | 0.125% |
| GMS** | — | — | — | 0.5% |
| Perfume | 0.25% | 0.25% | 0.25% | 0.75% |
| water & minors | | up to 100 | | |

*Polydimethylsiloxane
**glycerylmonostearate

Typically, the compositions above were prepared as follows:

The ditallowimidazole, and possibly the GMS and the ditallowdimethylammonium chloride are added in the molten form to a water seat containing the acid, under high shear mixing. Calcium chloride, PDMS, and perfume are then added and blended by stirring.

The compositions of example I to IV were found to be perfectly stable on storage.

We claim:

1. An imidazole compound of the formula:

$$HC=CH$$
$$| \quad |$$
$$N \quad N-X-R_2$$
$$\diagdown C \diagup$$
$$|$$
$$R_1$$

(I)

wherein $R_1$ and $R_2$ are, selected independently, $C_8$–$C_{30}$ alkyl or alkenyl groups; X is selected from the group of:

$$-R_3-O-C- \text{ and}$$
$$\quad \quad \quad \parallel$$
$$\quad \quad \quad O$$

$$-R_3-O-$$

wherein $R_3$ is a $C_2$–$C_5$ alkanediyl group or is $$(CH-CH_2-O)_n(CH_2-CH_2)_m$$
$$|$$
$$R_4$$

with n being an integer from 0 to 10, m an integer from 0 to 2, n+m>1, and $R_4$ being a $C_{1-4}$ alkyl group or hydrogen.

2. A compound in accordance with claim 1 wherein $R_1$ and $R_2$ are, selected independently, $C_{12}$–$C_{20}$ alkyl groups.

3. The compound of claim 2 wherein $R_1$ and $R_2$ are, selected independently, $C_{15}$–$C_{18}$ alkyl groups.

4. A compound in accordance with claim 2 wherein X is $$-R_3-O-C-$$
$$\quad \quad \quad \parallel$$
$$\quad \quad \quad O$$

and $R_1$ and $R_2$ are, selected independently, $C_{15}$–$C_{18}$ alkyl groups.

5. A compound in accordance with claim 4 wherein $R_3$ is ethanediyl.

6. A textile treatment composition in the form of stable aqueous dispersion, containing (a) from 1% to 40% by weight of an imidazole compound of the formula:

$$HC=CH$$
$$| \quad |$$
$$N \quad N-X-R_2$$
$$\diagdown C \diagup$$
$$|$$
$$R_1$$

(I)

wherein $R_1$ and $R_2$ are, selected independently, $C_8$–$C_{30}$ alkyl or alkenyl groups; X is selected from the group of:

$$-R_3-N-C-;$$
$$\quad | \quad \parallel$$
$$\quad R_4 \quad O$$

$$-R_3-O-C-;$$
$$\quad \quad \quad \parallel$$
$$\quad \quad \quad O$$

$$-R_3-; \text{ and}$$

$$-R_3-O-,$$

wherein $R_3$ is a $C_2$–$C_5$ alkanediyl group or is $$(CH-CH_2-O)_n(CH_2-CH_2)_m$$
$$|$$
$$R_4$$

with n being an integer from 0 to 10, m an integer from 0 to 2, n+m>1, and $R_4$ being a $C_{1-4}$ alkyl group or hydrogen, and (b) a dispersing aid selected from the group of Bronstedt acids having pKa value not greater than 6.

7. The composition according to claim 6 wherein the amount of dispersing aid is from 2% to 30% by weight of the imidazole compound.

8. The composition according to claim 6 comprising from 2% to 30% of the imidazole compound.

9. The composition of claim 6 wherein the dispersing aid is an acid selected from the group consisting of the inorganic mineral acids and the organic acids of the formula R—COOH or R—CH$_2$—SO$_3$H, and mixtures thereof.

10. The composition of claim 9 wherein the dispersing aid is formic acid, acetic acid, hydrochloric acid, gluconic acid, citric acid, phosphoric acid, benzoic acid, or methylsulfonic acid.

11. The composition according to claim 6 wherein the imidazole compound has the formula

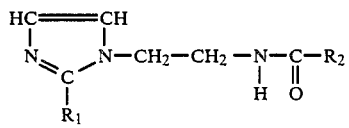

wherein R$_1$ and R$_2$ are, selected independently C$_{15}$–C$_{18}$ alkyl group.

12. The composition according to claim 6 wherein the imidazole compound has the formula

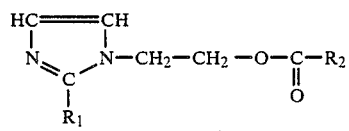

wherein R$_1$ and R$_2$ are, selected independently C$_{15}$–C$_{18}$ alkyl group.

13. The composition of claim 6 which additionally contains a quaternary ammonium softening compound.

14. The composition in accordance with claim 13 which contains from 0.5% to 15% by weight of quaternary ammonium softening compound, of the formula

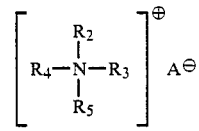

wherein R$_2$ is an acyclic aliphatic C$_{15}$–C$_{22}$ hydrocarbon group, R$_3$ is a C$_1$–C$_4$ saturated alkyl or hydroxyalkyl group, R$_4$ and R$_5$ are selected from R$_2$ and R$_3$; and A is an anion.

15. The composition in accordance with claim 6 which further comprises a co-softening agent selected from glycerol esters, fatty alcohols, alkoxylated fatty alcohols, and fatty acids.

16. The composition in accordance with claim 6 which further contains from 0–10% of an emulsion of polydimethyl siloxane having a viscosity at 25° C. of from 100 to 100,000 centistokes.

17. The composition according to claim 7 wherein the amount of dispersing aid is from 1% to 50% by weight of the imidazole compound.

* * * * *